United States Patent [19]

Butler et al.

[11] 4,383,826

[45] May 17, 1983

[54] ADDUCTS OF DIISOCYANATES AND METHACRYLOYL ALKYL ETHERS, ALKOXYBENZENES OR ALKOXYCYCLOALKANES, COMPOSITIONS CONTAINING SUCH COMPOUNDS, AND METHOD OF USE THEREOF

[75] Inventors: David V. Butler, West Covina; Patrick D. Kidd, San Dimas; Jan A. Orlowski, Altadena, all of Calif.

[73] Assignee: Blendax-Werke R.Schneider GmbH & Co., Fed. Rep. of Germany

[21] Appl. No.: 276,680

[22] Filed: Jun. 23, 1981

[30] Foreign Application Priority Data

Jul. 23, 1980 [EP] European Pat. Off. ........ 80104311.8

[51] Int. Cl.³ ............................................. A61K 6/08
[52] U.S. Cl. ..................................... 433/228; 106/35; 204/159.19; 204/159.23; 204/159.24; 260/998.11; 264/19; 433/199; 433/202; 433/226; 523/115; 523/116; 523/118; 524/264; 524/492; 526/301; 560/25; 560/115; 560/158

[58] Field of Search ............... 560/25, 115, 158; 526/301; 523/115, 116, 118; 260/998.11; 106/35; 204/159.19, 159.23, 159.24; 433/199, 201, 202, 212, 226, 228; 264/19; 524/264, 492

[56] References Cited

U.S. PATENT DOCUMENTS

| | | | |
|---|---|---|---|
| 3,425,988 | 2/1969 | Gorman et al. | 260/47 |
| 3,629,187 | 12/1971 | Waller | 260/42.44 |
| 3,801,344 | 4/1974 | Dietz | 106/300 |
| 3,975,203 | 8/1976 | Dietz | 106/299 |
| 3,979,426 | 9/1976 | DeMajistre | 560/158 |
| 4,017,649 | 4/1977 | DeMajistre | 560/115 |
| 4,065,627 | 12/1977 | Harrison | 560/115 |

*Primary Examiner*—Lorenzo B. Hayes
*Attorney, Agent, or Firm*—Jordan B. Bierman; Linda Bierman

[57] ABSTRACT

Polymerizable adducts of diisocyanates and methacryloyl alkyl ethers, alkoxybenzenes, or alkoxycycloalkanes are disclosed. The compounds of the present invention are formed into compositions which are useful as bone cement, fillings for cavities, and orthodontic adhesives. The compositions have improved mechanical properties, low water absorption, and excellent color and discoloration stability, coupled with a high filler content.

43 Claims, No Drawings

ADDUCTS OF DIISOCYANATES AND METHACRYLOYL ALKYL ETHERS, ALKOXYBENZENES OR ALKOXYCYCLOALKANES, COMPOSITIONS CONTAINING SUCH COMPOUNDS, AND METHOD OF USE THEREOF

This Application claims the priority of European Patent Application No. 80104311.8, filed on July 23, 1980.

The present invention is directed to polymerizable adducts of diisocyanates and methacrylol alkyl ethers, alkoxybenzenes, or alkoxycycloalkanes. It is also directed to the use of these compounds in binders or adhesives, as well as in dental restoration and filling material.

There are a number of polymerizable compounds already in existence having more than one double bond in the molecule. Such compounds are useful for various purposes, including binders for the production of adhesives, preparation of bone cements, dental restoration and filling compositions, dental sealing materials, orthopedic adhesives, and orthodontic adhesives.

The monomers of the present invention are especially well suited for the foregoing uses, especially those relating to medicine and dentistry.

The present invention comprises compounds of the formula

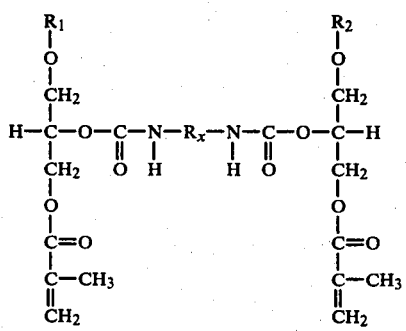

wherein $R_1$ and $R_2$ are individually a straight or branched chain, substituted or unsubstituted alkyl group having 1 to 14 carbon atoms, a substituted or unsubstituted aryl group, or a substituted or unsubstituted cycloalkyl group, and $R_x$ is a divalent aliphatic, cycloaliphatic, araliphatic, or aromatic radical having 2 to 14 carbons.

$R_1$ and $R_2$ can advantageously be methyl, ethyl, n-propyl, isopropyl, n-butyl, sec-butyl, t-butyl, pentyl, hexyl, heptyl, octyl, 2-ethylhexyl, nonyl, decyl, or lauryl. In particular, the 2-ethylhexyl radical is preferred. In addition, $R_1$ and $R_2$ may be substituted aromatic radicals; in particular, phenyl, benzyl, tolyl, xylyl, or cycloalkyl. In the last category, cyclohexyl is to be preferred.

$R_x$ is a straight or branched chain alkylene, divalent aromatic, araliphatic, or cycloalkylene. More specifically, ethylene, propylene, butylene, pentamethylene, hexamethylene, octamethylene, 2-ethylhexamethylene, phenylene, phenoxyphenylene, tolylene, methylene bisphenyl, propylene bisphenyl, cyclohexylene, methylene biscyclohexyl or propylene biscyclohexyl.

The preparation of the compounds of the present invention is carried out by condensation of the corresponding isocyanates with the appropriate methacryloylalkyl ethers, alkoxybenzenes, or alkoxycycloalkanes. These starting materials are, in turn, obtained by the reaction of methacrylic acid with suitable glycidyl ethers in a manner which is principally known. Suitable methods of preparation are described in DAS 2,357,324.

From the foregoing reference, as well as DOS 2,419,887 and U.S. Pat. No. 3,425,988, acrylic and methacrylic acid esters having carbaminic acid groups in the molecule are known. However, the compounds are structurally very different from the monomers of the present invention, and the advantages obtainable by the use of the present substances cannot be achieved.

The products of the present invention are useful for any purpose wherein monomers having at least two polymerizable double bonds in the molecule can be employed. As previously indicated, they are particularly suited for the use as binders and in adhesives, especially in medicine and dentistry.

In the latter, the present invention finds particular use in compositions used to fill teeth. These compositions, consisting of fillers and polymerizable compounds, have attained increasing importance in recent years. Such products are easy and safe to handle by the dentist, and are, as a rule, tolerated very well and without irritation by the patient. Moreover, such materials offer the possibility of avoiding the use of amalgams which have been criticized on repeated occasions for physiological reasons.

The disadvantages of the prior art compositions, compared to conventional filling materials, are their susceptibility to shrinkage and their water absorption. The shrinkage will permit the formation of secondary cavities in the tooth between the edge of the filling and the original cavity wall. Such a drawback is quite serious since the filling can actually increase the opportunity for further cavities to form.

It is, therefore, among the objects of the present invention to overcome the foregoing problems of prior compositions and to provide materials which minimize shrinking, exhibit little water absorption, offer good mechanical properties, and are color-stable. Such properties can be achieved by maintaining a very high proportion of filler material in the finished compositions. The maximum quantity of filler possible depends upon the properties of the monomers used in the composition. Known compositions evidence, after hardening, approximately the following mechanical properties.

Water absorption at 37° C.: 0.7–1.2 mg/cm$^2$ (*)
Compressive strength: 30,000 to 40,000 psi
Diametric tensile strength: 3,480 to 4,200 psi
Hardness (Barcol): 98
Color stability: no color change detectable (*)
Opacity/translucency factor: 0.35 to 0.55 (*)
Weight ratio filler to resin: 3.5:1 to 4.2:1

(*)determined according to the Specification No. 27 described in the "Journal of the American Dental Assoc.", Vol. 94 (June 1977).

It has been found that the foregoing properties of existing compositions can be very substantially improved by the use of the monomers of the present invention. In particular, a much higher ratio of filler to resin can be obtained, thus producing the desired results. More specifically, compositions having up to 90% filler can be obtained by the incorporation of the monomers of the present invention.

The dental filling compositions of the present invention contain at least one of the monomers of the present invention, a filler, a polymerization initiator or an accelerator, as well as the usual additives; e.g. additional monomers, UV absorbers, stabilizers, dyes, etc.

The filling materials may be transparent or opaque to X-rays. In particular, silicon dioxide based materials have been found particularly useful. Glass (pulverized), borosilicate glass, guartzite, christobalite, barium-aluminium silicate, lithium-aluminium silicate, or glass ceramic materials (containing, for example, lanthanum or zirconium) are satisfactory. Suitable opaque fillers are exemplified by U.S. Pat. Nos. 3,801,344; 3,808,170; and 3,975,203; as well as DOS 2,347,591. In order to increase adhesivity, the fillers may be silanized in the usual manner.

The preferred particle sizes of the fillers ranges between 0.01 and 100 microns. It has also been found possible and useful to use combinations of fillers of low and high particle sizes. The preferred particle diameter is about 0.05 to about 50, most preferably about 30 microns.

The compositions of the present invention lend themselves to two modifications; either two-phase preparations, or single phase preparations. In the former case, one phase will contain a polymerization initiator and the other will contain an accelerator therefor. Suitable initiators are generally peroxides, while accelerators are organic amines. In this case, the two phases are brought together just prior to filling the tooth. The polymerization occurs in the drilled cavity to be filled, which is preferably provided with a lining material.

On the other hand, the single phase preparations polymerize under the action of light; e.g. UV or laser beams. Such compositions will contain a photo-polymerization initiator and, preferably, an accelerator. The monomers of the present invention are suitable in both types of compositions.

In the single phase preparations, suitable photo-polymerization initiators are generally known and are usually carbonyl compounds. In particular, benzil and benzil derivatives (such as 4,4-oxydibenzil) or other dicarbonyl compounds such as diacetyl, 2,3-pentanedione, or metal carbonyls, quinones and derivatives thereof can be used. Advantageously, the initiator constitutes about 0.01 to about 5.0% by weight of the total composition. Preferably, these single-phase preparations also contain polymerization accelerators, which accelerate the polymerization reaction in the presence of the initiators.

Suitable accelerators are, for example, amines such as p-toluidine, dimethyl-p-toluidine, trialkylamines, polyamines (such as N,N,N',N'-tetra-alkyl-alkylene diamines) and sulfimides. These accelerators preferably are about 0.01 to about 5% by weight of the total composition.

In the two-phase embodiment of the invention, the phases must be kept separated from each other until they are ready for use. As a rule, such mixtures will contain a polymerization initiator which is usually a peroxide. When polymerization is initiated, these peroxides decompose to form radicals. Suitable peroxides are aryl peroxides (such as benzoyl peroxide, cumene hydroperoxide, urea peroxide, t-butyl hydroperoxide, or t-butyl perbenzoate) and silyl peroxides. For best results, these should be used in the range of about 0.01 to about 5.0% by weight based on the total composition. The more preferred range is from about 0.5 to 2.5% by weight.

It has been found particularly useful to place the polymerization initiator in one of the two phases and the accelerator (preferably an amine) in the other phase.

It has also been found expedient to include polymerizable organo-silicon compounds which may be added to the composition in order to improve the adhesivity between the filler and the resin. Such materials as methacryloyl-alkyl-trihydroxy silanes or methacryloyl-trimethoxy silanes are particularly suitable. The polymerizable silane materials may be also reacted in known manner with the filler material.

It is also possible to include other monomers in the inventive compositions. Such monomers are generally well known and their properties are equally known. Typical of such additional additives are are alkanediol dimethacrylates, reaction products of bisphenols (particularly bisphenol A) and glycidyl methacrylate (hereinafter bis-GMA), etc.. More specifically, such materials are 1,6-hexanediol dimethacrylate; 1,4-butanediol dimethacrylate; triethylene-glycol dimethacrylate; tetra-ethylene-glycol dimethacrylate; bis-(2-methacryloylethyl)-phthalate; bis-(2-methacryloylethyl)-isophthalate, bis-(2-methacryloylethyl)terephthalate, trimethylolpropane dimethacrylate, trimethylolpropane trimethacrylate, reaction products of diisocyanates and simple hydroxyalkyl methacrylates, adducts of (di) isocyanates and 2,2-propane bis-3-(4-phenoxy)-1,2-hydroxy-propane-1-methacrylate, etc. The diisocyanate-hydroxyalkyl methacrylates are described in DOS 2,312,559 and the adducts of (di) isocyanates and the named methacrylate compounds are set forth in U.S. Pat. No. 3,629,187. Of course, the foregoing list is intended to be exemplary only, and other known polymerizable compounds can be used for this purpose.

It is also possible to include minor amounts of UV stabilizers; such as hydroquinone, p-benzoquinone, p-butyl-hydroxytoluene and the like. In addition, the inclusion of appropriate dyes are included to give the filled areas as natural an appearance as possible.

A survey of the compounds and methods used in the prior art for the preparation of dental filling (composite) materials is given in Journal of Dental Research, Vol. 58/No. 5 (1979), p. 1493-1506; the disclosure of this article is to be included.

The following examples will illustrate the invention.

EXAMPLE A 225 g phenyl glycidyl ether are reacted with 150 g methacrylic acid at 100° C. in the presence of 1 g triphenyl phosphine and 0.7 g di-t-butyl-p-hydroxytoluene under stirring until an epoxy equivalent of less than 0.005 is reached.

After distillation of the unreacted excess methacrylic acid until to the point at which the acid number is below 3, the remaining residue is cooled to 40° C. and an equimolar quantity of methylene-bis-(4-isocyanatocyclohexane) is added over a period of one hour at 45°–50° C. The mixture is left standing overnight at 30° C. The resulting carbamate is a light yellow liquid having a refractive index of 1.528 at 30° C.

In an analogous manner the corresponding cyclohexyl derivative can be prepared by substituting cyclohexyl glycidyl ether for the phenyl glycidyl ether.

EXAMPLE B

A reaction product is obtained in a manner similar to that of Example A from 150 g phenyl glycidyl ether and 129 g methacrylic acid and is reacted with 84 g hexamethylene diisocyanate for one hour at 45°–50° C. After standing overnight at 30° C., a pale yellow viscous liquid, consisting of the hexamethylene biscarbamate of 3-methacroyl-2-hydroxypropoxybenzene, is obtained.

EXAMPLE C 185.34 g 2-ethylhexylglycidyl ether and 129 g methacrylic acid are reacted at 100° C. in the presence of 2 g triphenyl phosphine, under vigorous agitation, until the reaction mixture shows an epoxy equivalent of less than 0.005.

After the distillation of the excess methacrylic acid to a point at which the acid number is less than 3, the mixture is cooled to 40° C. and, over a period of 1 hour, 131 g methylenebis-(4-isocyanatocyclohexane) are added at 45°–50° C. The reaction product is then kept overnight at 30° C. The reaction product is a pale yellow viscous liquid having a refractive index of 1.543 at 30° C.

EXAMPLE 1

A filling material is prepared from the following components:

| Paste A | | Paste B | |
|---|---|---|---|
| Pulverized quartz | 200 parts | Pulverized quartz | 200 parts |
| Pulverized glass | 320 parts | Pulverized glass | 320 parts |
| Methacroylpropyl trihydroxysilane | 4 parts | Methacroylpropyl trihydroxysilane | 4 parts |
| Benzoyl peroxide | 2.5 parts | N,N—diethanol-p-toluidine | 4 parts |
| Bis-GMA | 72 parts | UV absorber (Cyasorb$^R$) | 1 part |
| 2,2-Bis-4'-(2"-methacroylethoxy-)phenyl- propane | 66 parts | Monomer acc. to Example C | 70 parts |
| Triethyleneglycol dimethacrylate | 22 parts | Hexanediol dimethacrylate | 30 parts |

Pastes A and B are mixed together in equal parts and briefly hardened; the product obtained shows the following mechanical properties:
Water absorption at 37° C.: 0.51 mg/cm$^2$
Diametric tensile strength: 6100 psi
Compressive strength: 38000 psi
Hardness (Barcol): 100
Opacity/translucency factor (C$_{70}$): 0.4
Moreover, excellent color stability is obtained.

EXAMPLE 2

A filling material consists of two pastes of the following composition:

| Paste A | | Paste B | |
|---|---|---|---|
| Pulverized glass | 500 parts | Pulverized glass | 500 parts |
| Methacroylpropyl trihydroxysilane | 4 parts | Methacroylpropyl trihydroxysilane | 4 parts |
| Benzoyl peroxide | 2.5 parts | N,N'—diethanol-p-toluidine | 4 parts |
| Monomer acc. to Example B | 75 parts | UV absorber (Cyasorb$^R$) | 1 part |
| Hexandediol dimethacrylate | 25 parts | Monomer acc. to Example B | 75 parts |
| | | Hexandiol dimethacrylate | 25 parts |

Pastes A and B are mixed together in approximately equal amounts and are completely hardened after about 2.5 minutes at 23° C. The polymerization product shows the following physical values:

Water absorption at 37° C.: 0.45 mg/cm$^2$
Diametric tensile strength: 6200 psi
Compressive strength: 40000 psi
Hardness (Barcol): 100
The product evidences excellent color stability and an attractive, natural appearance.

EXAMPLE 3

A filling material consisting of two pastes is prepared as follows:

| Paste A | | Paste B | |
|---|---|---|---|
| Pulverized glass | 500 parts | Silica | 500 parts |
| Methacroylpropyl trihydroxysilane | 4 parts | Methacroylpropyl trihydroxysilane | 4 parts |
| Benzoyl peroxide | 2.5 parts | N,N—diethanol-p-toluidine | 4 parts |
| Monomer acc. to Example A | 70 parts | UV absorber | 1 part |
| Triethyleneglycol dimethacrylate | 30 parts | Monomer acc. to Example A | 70 parts |
| | | Hexandiol dimethacrylate | 30 parts |

Pastes A and B are mixed in approximately equal parts. Hardening occurs at 23° C. in 150 seconds. The hardened material shows the following properties:
Water absorption at 37° C.: 0.45 mg/cm$^2$
Diametric tensile strength: 6500 psi
Compressive strength: 40500 psi
Hardness (Barcol): 100
The color stability was excellent.

EXAMPLE 4

A radio opaque, light-hardening single-phase filling material of the following composition is prepared:
Titanium silicate (mean particle size 0.1–5 microns): 190 parts
Lithium aluminium silicate (mean particle size 5–25 microns): 700 parts
Acetophenone: 3 parts
N,N-dimethyl-p-toluidine: 5 parts
Adduct from methacryloyloxypropoxyhydroxycyclohexane and tolylene diisocyanate: 80 parts
Bis-GMA: 26 parts

EXAMPLE 5

A fissure sealing material is prepared according to the following monomer composition:
Monomer according to Example A: 50%
Triethyleneglycol dimethacrylates: 20%
1,6-Hexanediol dimethacrylate: 30%
The hardening of this resin mixture can be effected either by a redox system (e.g. cumene peroxide/triarylamine) or by radiation with UV light or visible light in the presence of a UV activator such as benzoin, benzoin methyl ether, benzil, etc.

EXAMPLE 6

Dental lacquer:
Adduct of hexamethylene diisocyanate and 3-methacroyloxy-2-hydroxypropoxytoluene: 75%
2-ethylhexyl methacrylate: 10%
Glycol dimethacrylate: 14.5%
Benzoin methyl ether: 0.5%

Although only a limited number of specific embodiments of the present invention have been expressly disclosed, it is, nonetheless, to be broadly construed and not to be limited except by the character of the claims appended hereto. In particular, the monomers, according to this invention are useful in any situation wherein those with more than one double bond in the molecule are presently employed, particularly in binders useful in medicine or dentistry.

What we claim is:

1. A compound of the formula:

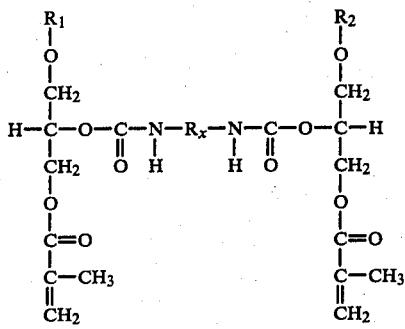

wherein $R_1$ and $R_2$ are individually straight or branched chain, substituted or unsubstituted alkyl groups having 1 to 14 carbon atoms, a substituted or unsubstituted aryl group, or a substituted or unsubstituted cycloalkyl group, and $R_x$ is a divalent, aliphatic, cycloaliphatic, araliphatic, or aromatic radical having 2 to 14 carbon atoms.

2. A compound of claim 1 wherein $R_1$ and $R_2$ are taken from the class consisting of methyl, ethyl, n-propyl, isopropyl, n-butyl, sec-butyl, tert-butyl, pentyl, hexyl, heptyl, octyl, 2-ethylhexyl, nonyl, decyl, lauryl, phenyl, benzyl, tolyl, xylyl, and cyclohexyl.

3. A compound of claim 1 wherein $R_x$ is taken from the class consisting of ethylene, propylene, butylene, pentamethylene, hexamethylene, octamethylene, 2-ethylhexamethylene, phenylene, phenoxyphenylene, tolylene, methylene bisphenyl, propylene-bisphenyl, cyclohexylene, methylene-biscyclohexyl, and propylenebiscyclohexyl.

4. A compound of claim 1 wherein $R_1$ and $R_2$ are 2-ethylhexyl.

5. A compound of claim 1 wherein $R_1$ and $R_2$ are alkyls having 2 to 8 carbon atoms, and $R_x$ is hexamethylene.

6. A compound of claim 1 wherein $R_1$ and $R_2$ are alkyls having 2 to 8 carbons, and $R_x$ is phenylene or tolylene.

7. A compound of claim 1 wherein $R_1$ and $R_2$ are alkyls having 2 to 8 carbons, and $R_x$ is cycloalkylene or methylenebiscycloalkyl.

8. A compound of claim 5 wherein $R_1$ and $R_2$ are 2-ethylhexyl.

9. A compound of claim 1 wherein $R_1$ and $R_2$ are substituted or unsubstituted phenyl, and $R_x$ is hexamethylene.

10. A compound of claim 1 wherein $R_1$ and $R_2$ are substituted or unsubstituted phenyl, and $R_x$ is phenylene or tolylene.

11. A compound of claim 1 wherein $R_1$ and $R_2$ are substituted or unsubstituted phenyl, and $R_x$ is cycloalkylene or methylenebiscycloalkyl.

12. A compound of claim 1 wherein $R_1$ and $R_2$ are substituted or unsubstituted cycloalkyl, and $R_x$ is hexamethylene.

13. A compound of claim 2 wherein $R_1$ and $R_2$ are cyclohexyl.

14. A compound of claim 1 wherein $R_1$ and $R_2$ are substituted or unsubstituted cycloalkyl, and $R_x$ is phenylene or tolylene.

15. A compound of claim 14 wherein $R_1$ and $R_2$ are cyclohexyl.

16. A compound of claim 1 wherein $R_1$ and $R_2$ are substituted or unsubstituted cycloalkyl, and $R_x$ is cycloalkylene or methylenebiscycloalkyl.

17. A compound of claim 16 wherein $R_1$ and $R_2$ are cyclohexyl.

18. A composition comprising a compound of claim 1 and a filler.

19. A composition of claim 18 containing a filler, 10 to 50% by weight of said compound and 0,1 to 5% by weight of a polymerization initiator or accelerator.

20. A composition of claim 18 wherein there are also present at least one UV absorber, dye, adhesion improver, or additional polymerizable substances.

21. A method of filling cavities in teeth comprising introducing a composition containing a compound of claim 1 into said cavities and causing said composition to set.

22. A method of producing prosthetic teeth comprising forming a composition containing a compound of claim 1 into the shape of a tooth, and causing said composition to set.

23. A method of claim 21 or 22 wherein said composition is set by application of UV radiation.

24. A compound of claim 1 wherein $R_x$ is alkylene, cycloalkylene, aralkylene, or aromatic.

25. A composition of claim 18 or 19 wherein said filler has a particle size of 0.01 to 100 microns.

26. A composition of claim 25 wherein said size is 0.05 to 50 microns.

27. A composition of claim 19 wherein said initiator is activated by UV or laser radiation.

28. A composition of claim 27 wherein said initiator is a dicarbonyl or a metal carbonyl compound.

29. A composition of claim 28 wherein said initiator is benzil or derivatives thereof, diacetyl, 2,3-pentadione, quinone, or quinone derivatives.

30. A composition of claim 29 wherein said benzil derivative is 4,4-oxybenzil.

31. A composition of claim 19 wherein said initiator is about 0.01 to about 5.0% by weight of said composition.

32. A composition of claim 19 wherein said accelerator is p-toluidine, dimethyl-p-toluidine, trialkylamines, or polyamines.

33. A composition of claim 32 wherein said polyamines are N,N,N',N'-tetraalkylalkylene diamines.

34. A composition of claim 19 wherein said accelerator is about 0.01 to 5.0% by weight of said composition.

35. A composition comprising a first mixture containing a polymerization initiator, a second mixture containing a polymerization accelerator, a compound of claim 1 in at least one of said mixtures, and a filler in at least one of said mixtures.

36. A composition of claim 35 wherein said initiator is a peroxide.

37. A composition of claim 35 wherein said initiator is aryl peroxide or silyl peroxide.

38. A composition of claim 36 wherein said peroxide is benzoyl peroxide, cumene hydroperoxide, urea peroxide, t-butyl hydroperoxide, t-butylperbenzoate, or a silyl peroxide.

39. A composition of claim 36 wherein said peroxide is 0.01 to 5.0% by weight of said composition.

40. A composition of claim 39 wherein said peroxide is 0.5 to 2.5% by weight of said composition.

41. A composition is claim 35 wherein at least one of said first mixture and said second mixture contains a polymerizable organo-silicon compound.

42. A composition of claim 41 wherein said organo-silicon compound are methacryloyl-alkyltrihydroxy silanes or methacryloyl-trimethoxy silane.

43. A composition of claim 26 wherein said size is about 30 microns.

* * * * *